United States Patent [19]
Catot et al.

[11] Patent Number: 5,349,861
[45] Date of Patent: Sep. 27, 1994

[54] DEVICE FOR AUTOMATICALLY MEASURING THE RESIDUAL STRESSES IN THE RIM OF ONE WHEEL OF A RAILWAY WHEELSET

[75] Inventors: Bernard Catot, Leffrinckoucke; Valério Del Fabbro, Marly; Guy Stevenot, Denain, all of France

[73] Assignee: Valdunes, Puteaux, France

[21] Appl. No.: 11,154

[22] Filed: Jan. 29, 1993

[30] Foreign Application Priority Data

Mar. 30, 1992 [FR] France ............................. 92 03817

[51] Int. Cl.⁵ .......................................... G01N 29/04
[52] U.S. Cl. .......................................... 73/598; 73/624
[58] Field of Search .................. 73/597, 593, 624, 649, 73/658, 661, 598, 636

[56] References Cited

U.S. PATENT DOCUMENTS 3,596,503 8/1971 Gay ........................................ 73/625
3,978,712 9/1976 Cowan ................................ 73/631 X

FOREIGN PATENT DOCUMENTS 2105845 3/1983 United Kingdom ................. 73/649

*Primary Examiner*—Hezron E. Williams
*Assistant Examiner*—Christine K. Oda
*Attorney, Agent, or Firm*—Oblon, Spivak, McClelland, Maier & Neustadt

[57] ABSTRACT

The wheel rests upon a rail. A chassis mounted on a lifting and supporting mechanism carries slides arranged on either side of the rail and parallel to the rail. Two carriages are mounted to move translationally on the slides. Grinding devices, an ultrasound checking device and two position detectors are mounted on the carriages to move translationally in a direction perpendicular to the slides. The propagation time for the ultrasound in the rim is measured in two perpendicular directions and the width of the rim is measured. The propagation speeds of the ultrasound are calculated and compared so as to determine the stressed state of the rim.

9 Claims, 2 Drawing Sheets

DEVICE FOR AUTOMATICALLY MEASURING THE RESIDUAL STRESSES IN THE RIM OF ONE WHEEL OF A RAILWAY WHEELSET

BACKGROUND OF THE INVENTION

1. Field of the Invention

The invention relates to checking the residual stresses in wheels equipping railway wheelsets.

2. Discussion of the Background

At regular time intervals the wheels equipping railway wheelsets are subjected to checks which especially consist in measuring the residual stresses in the rims.

In order to do that, the surface of the rims is locally ground. A transverse-wave ultrasound feeler, oriented in a first direction then oriented in a perpendicular direction is applied to the ground surface, the thickness of the rim is measured and the difference in speed of the ultrasonic waves between the two perpendicular orientations is determined.

All these operations are carried out manually and are relatively slow, which is a drawback when there are a great number of wheels to be checked.

SUMMARY OF THE INVENTION

The object of the present invention is to overcome this drawback by proposing an automatic means for carrying out checks on the rims of railway wheels.

For this purpose, the subject of the invention is a device for automatically measuring the residual stresses in the rim of one wheel of a railway wheelset comprising two wheels each resting upon a rail, characterised in that it comprises:

the rail for supporting the wheel, lifting and supporting means resting upon a substantially horizontal surface situated at a lower level than the rail and arranged substantially vertically above the rail, a chassis mounted on the lifting and supporting means, so as to be adjustable vertically, two sets of slides fixed to the chassis in a direction parallel to the rail, arranged on either side of the rail, two carriages mounted to move translationally on the slides, means for displacing the carriages, two grinding devices, each carried by a carriage and mounted to move on the carriage, in a direction perpendicular to the slides, means for displacing the grinding devices, an ultrasound checking device mounted to move translationally on one of the two carriages, in a direction perpendicular to the slides, means for displacing the ultrasound checking device between a service position in contact with the rim of the wheel and a withdrawn position, two position detectors of the mechanical type, each mounted to move on a carriage, in a direction perpendicular to the slides and means for displacing the detectors between a non-obstructing position and a position bearing against the rim of the wheel, the two detectors being located facing one another on either side of the wheel.

Preferably, the means for lifting and supporting the chassis are screw jacks synchronized with one another and the means and devices for translationally displacing the carriages, the grinding devices, the ultrasound checking device and the mechanical position detectors are pneumatic jacks.

The ultrasound checking device comprises a head for emitting and receiving transverse ultrasound waves mounted rotationally about a horizontal axis parallel to the axis of displacement of the ultrasound checking device, a means for rotating the emitting and receiving head and a means for distributing coupling fluid.

Preferably, the means for rotating the emitter-receiver head is a quarter-of-a-turn pneumatic jack and the means for distributing coupling fluid is a metering pump extended by a tube opening out in line with the emitter-receiver head.

The device further comprises electropneumatic and electronic control means. Preferably, the electronic control means is a microprocessor.

The rail which is situated above the device comprises, in line with the device, a V-shaped nick on its upper part.

This device makes it possible automatically and rapidly to check residual stresses in the rim of a wheel of a railway wheelset.

BRIEF DESCRIPTION OF THE DRAWINGS

The invention will now be described in more detail with reference to the appended figures, in which.

DESCRIPTION OF THE PREFERRED EMBODIMENTS

Figure 1:
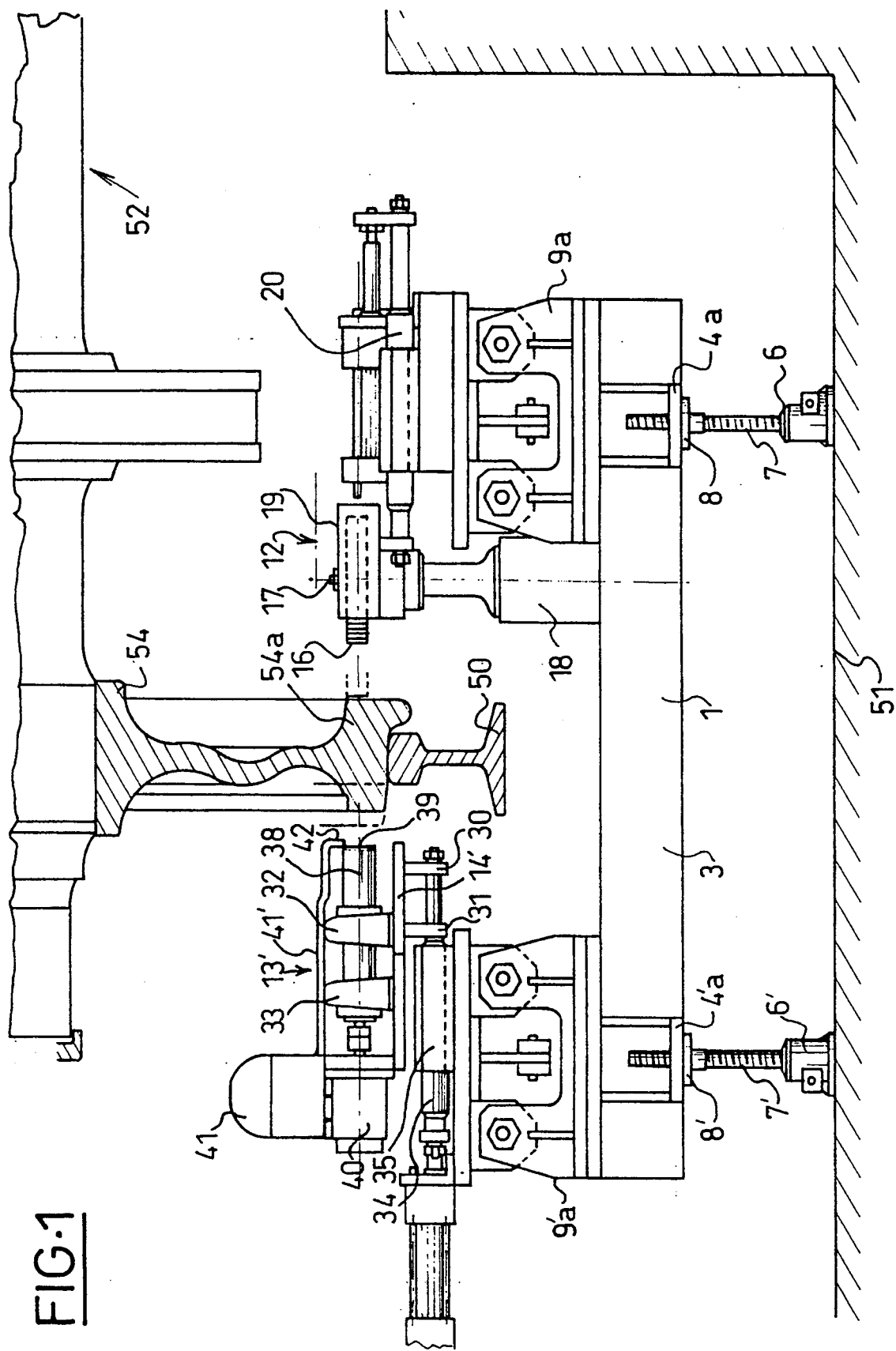
FIG. 1 is an elevational view of the device according to the invention.

The device according to the invention comprises a rectangular chassis 1 consisting of two longitudinal beams 2, 2' and two transverse beams 3, 3'. The longitudinal beams 2 and 2' extend beyond the transverse beams 3 and 3', in order to form supports 4a, 4b, 4'a, 4'b pierced with holes 5a, 5b, 5'a, 5'b. The chassis 1 is placed on four screw jacks 6, 6' (only two can be seen in FIG. 1) whose screws 7, 7' pass through the holes 5a, 5b, 5'a, 5'b.

By means of the supports 4a, 4b, 4'a, 4'b, the chassis 1 rests on the nuts 8, 8' of the screw jacks. These nuts are fixed by screws, not shown, to the supports 4a, 4b, 4'a, 4'b.

The screws of the screw jack may be rotated by motors, not shown, equipped with a control device. They are synchronized with one another. Each longitudinal beam 2, 2' carries two slides 8a, 8b, 8'a, 8'b parallel to the beams and held by supports 9a, 9b, 9'a, 9'b fixed by screws, not shown, to the longitudinal beams. The slides extend substantially over the entire length of the space between the transverse beams.

Each series of slides 8a, 8b and 8'a, 8'b carries a sliding carriage 10, 10'. For each carriage-slide assembly, a pneumatic jack 11, 11' fixed, on the one hand, to the chassis and, on the other hand, to the carriages, translationally displaces the corresponding carriage.

Figure 2:
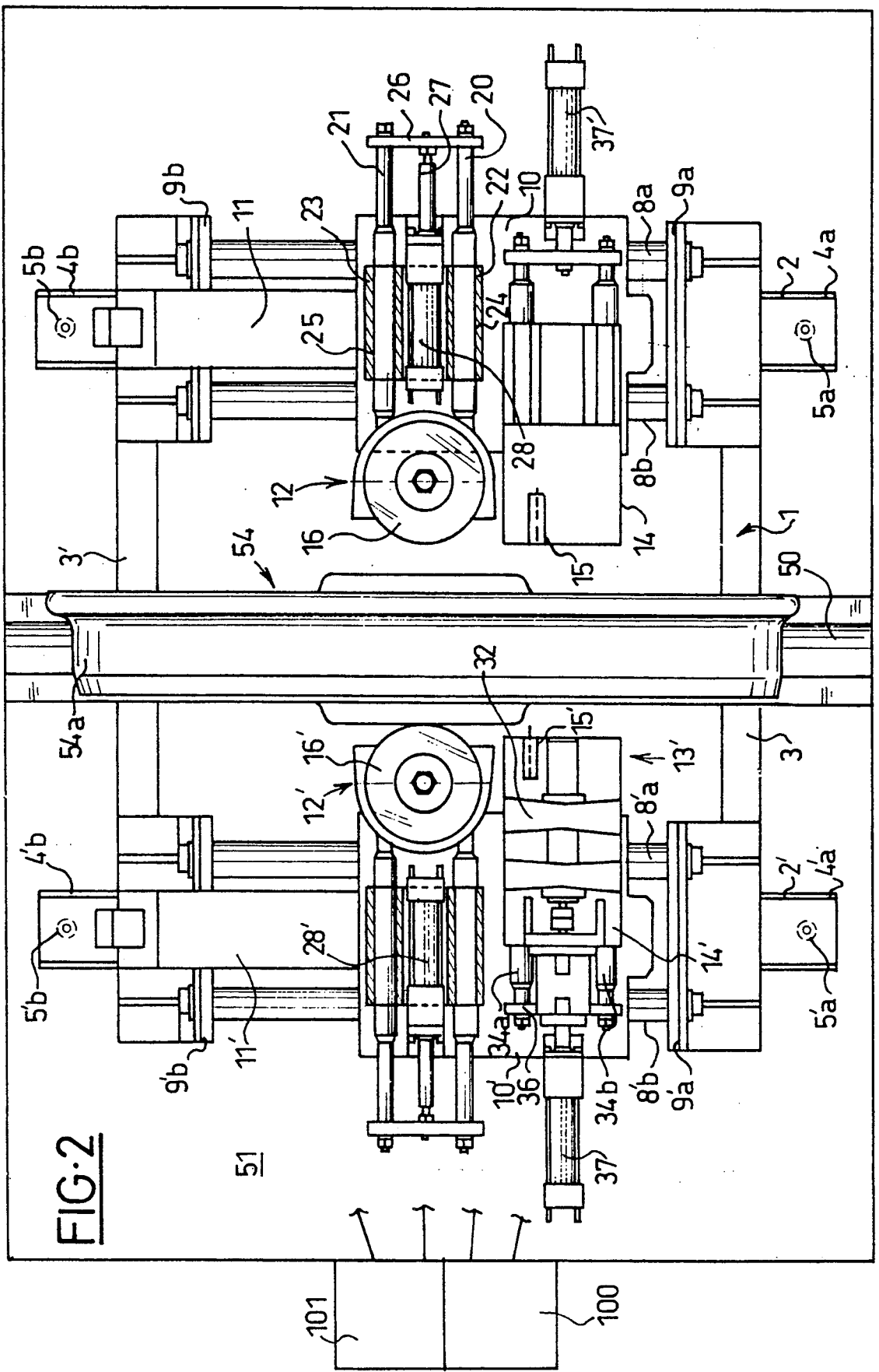
FIG. 2 is a top plan view thereof.

The carriage situated to the left in FIG. 2 carries a grinding device 12' mounted slidingly and an ultrasound checking assembly 13' mounted on a sliding support 14'; the grinding device and the sliding support are mounted to move translationally in a direction perpendicular to the direction of the slides 8'a, 8'b.

The carriage situated to the right in FIG. 2 carries a grinding device 12 identical to the grinding assembly 12' but arranged symmetrically with respect to the median plane of the machine parallel to the slides 8a, 8b, 8'a, 8'b. This carriage also carries a sliding support 14 identical to the support 14' but arranged symmetrically with respect to the axis of the machine.

The supports 14 and 14' carry position detectors consisting of mechanical feelers 15 and 15' whose position is identified by optical rules whose signals may be sent to a microprocessor.

Since the two grinding devices are identical, only one of them, the right-hand assembly, will be described.

The grinding device 12 comprises a disc-shaped grinding wheel 16 mounted rotationally about a spindle 17 driven by a motor 18. The grinding wheel 16 is partially surrounded by a hood 19. The motor assembly is fixed to two rods 20 and 21 mounted slidingly in the carriage 10.

The carriage 10 comprises two projecting parts 22 and 23 pierced with holes 24 and 25 in which the rods 20 and 21 slide. These rods slide in a direction perpendicular to the slides 8a, 8b and parallel to the bearing plane of the chassis.

On the side opposite the grinding wheel 16, the rods 20 and 21 are connected by a crosspiece 26 to which is fixed the end of the rod 27 of a pneumatic jack 28 fixed to the carriage 10.

The supports 14 and 14' are identical. Only the support 14' and its mounting will be described, this support 14' carrying the ultrasound checking device.

The support 14' is a rectangular plate equipped, at its lower part, with four lugs 30, 31 (only two are visible) and at its upper part with two bearings 32, 33. Two rods 34a and 34b are fixed to the lugs 30 and 31 and slide in projecting parts 35 (only one of which is visible) of the bed 10'. The rods 34a, 34b are connected at one of their ends by a crosspiece 36 to a pneumatic jack 37. The body of this jack is fixed to the bed 10' and allows the support 14' to be translated perpendicularly to the direction of the slides 8'a, 8'b.

A transverse-wave ultrasound checking device 38 of cylindrical shape is engaged in the bearings 32 and 33 so as to able to revolve on itself about its axis. This device has, at one of its ends, an active head 39 for emitting and receiving transverse ultrasonic waves. The other end is connected to a quarter-of-a-turn pneumatic jack 40. Above the jack there is placed a metering pump 41 whose delivery is extended by a tube 41' whose end 42 opens out in the vicinity of the active head 39.

The grinding wheels, the active head of the ultrasound checking device, and the mechanical feelers are all placed in the same plane parallel to the plane of the chassis 1.

The jacks and measuring means assembly are connected to electropneumatic device 100 and electronic device 101 which make it possible to perform all the movements automatically.

The device described rests, by means of screw jacks 6, 6', on a horizontal surface 51 under a rail 50 of a railway track. This rail 50 comprises a V-shaped nick. The rail 50 is in the axis of the machine and parallel to the slides 8a, 8b, 8'a, 8'b. The nick in the rail is more or less in the middle of the device.

In order to perform a check, the procedure is as follows:

by causing it to run on the railway track, a wheelset 52 is brought and stopped when one of the wheels 54 is in the V-shaped nick; the wheelset is thus positioned with respect to the machine;

the height of the chassis 1 is adjusted with the aid of the screw jacks 6, 6' so that the grinding wheels, the ultrasound checking device and the mechanical feelers are at the height of the rim 54a of the wheel 54.

The grinding wheels 16, 16' are brought opposite the rim of the wheel with the aid of the jacks 11 and 11'.

The grinding wheels 16, 16' which rotate on the rim 54a of the wheel 54 are applied with the aid of the jacks 28, 28' and simultaneously, with the aid of the jacks 11 and 11', the grinding wheels are made to carry out a slight reciprocating movement, then the grinding wheels are moved away from the rim.

The feelers 15, 15' are brought to face the ground zone of the rim with the aid of the jacks 11 and 11' and the feelers are applied against the rim with the jacks 37 and 37'; the position of the feelers is measured, which makes it possible to determine the thickness of the rim, which is recorded; then the feelers are moved away.

The ultrasound checking head 39 is brought to face the ground zone with the aid of the jacks 11 and 11', a small amount of coupling liquid is sent with the aid of the metering pump 41, then the checking head is applied to the rim with the aid of the jack 37 and a first measurement is made of the ultrasound propagation time, the result of which is recorded, then the quarter-of-a-turn pneumatic jack 40 is used to turn the checking device through a quarter of a turn then a second measurement is made whose result is recorded, the ultrasound measuring device is then moved away from the rim of the wheel.

The checking principle consists in determining the propagation speed of the ultrasonic waves in the thickness of the rim and in two mutually perpendicular vibration directions, which, by comparison, makes it possible to determine the amplitude of the residual stresses.

The reader will understand that the device which has just been described may be produced by equivalent means, in particular for guiding and moving the various movable elements.

The vertical positioning of the chassis may be produced automatically by using, for example, an inductive detector arranged, for example, on the support 14.

I claim:

1. A device for measuring the residual stresses in a rim of one wheel of a railway wheelset having two wheels each resting upon a horizontal rail, said device comprising:

the rail for supporting the wheel, a mechanism for lifting and supporting a chassis, said lifting and supporting mechanism resting upon a substantially horizontal surface situated at a level lower than the rail and having a plurality of substantially vertically extending parts arranged under the rail, wherein said chassis comprises a horizontal chassis mounted on the mechanism for lifting and supporting so as to be adjustable in height on the vertical parts, two sets of slides fixed to the chassis in a direction parallel to the rail and wherein one of said sets of slides is on one side of the plane of symmetry of the rail and the other said sets of slides is on the other side of the plane of symmetry of the rail, a carriage mounted to move translationally on each one of said sets of slides, a mechanism for translationally displacing each said carriage on said slides, a grinding device mounted on each said carriage for moving in a direction perpendicular to the slides at a level for allowing the grinding device to grind the rim of the wheel, a mechanism for displacing each said grinding device towards and away from the wheel, an ultrasound checking device mounted to move translationally on one of the two carriages in a direction perpendicular to the slides, a mechanism for displacing the ultrasound checking device between a service position in contact with the rim to measure the residual stresses in the rim of the wheel and a position withdrawn from the rim, a position detector mounted on each said carriage for moving in a direction perpendicular to the slides, a mechanism for displacing each said detector between a non-obstructing position and a position bearing against the rim of the wheel, each said detector located facing one another to measure the thickness of the rim.

2. The device according to claim 1, wherein the mechanism for lifting and supporting the chassis comprise screw jacks connected so that the screws of the jacks move vertically in a synchronized manner.

3. The device according to claim 1, wherein each said mechanism for displacing each said carriage, each said grinding device, the ultrasound checking device and each said position detector comprise pneumatic jacks.

4. The device according to claim 1, wherein the ultrasound checking device comprises a head for emitting and receiving transverse ultrasound waves which is mounted rotationally about a horizontal axis perpendicular to the slides, a mechanism for rotating the emitting and receiving head and a mechanism for distributing coupling fluid between the head of the ultrasound checking device and the rim of the wheel.

5. The device according to claim 4, wherein the mechanism for rotating the head of the ultrasound checking device comprises a quarter-of-a-turn pneumatic jack.

6. The device according to claims 4 or 5, wherein the mechanism for distributing coupling fluid comprises a metering pump extended by a tube opening out in line with the emitting and receiving head.

7. The device according to claim 1, wherein each said mechanism for displacing each said carriage, the grinding device, the ultrasound checking device and each said position detector and the ultrasound checking device comprise one of an electro-pneumatic and electronic control mechanism.

8. The device according to claim 7, wherein the electronic control mechanism comprises a microprocessor.

9. The device according to claim 1, wherein the rail includes an upper part on which is arranged a V-shaped nick for stopping the wheel at a measuring and checking position for measuring the residual stresses in the rim.

* * * * *